United States Patent [19]

Tews

[11] Patent Number: 4,792,326

[45] Date of Patent: Dec. 20, 1988

[54] RAPIDLY DISINTEGRATING PAPER TUBES

[75] Inventor: Richard R. Tews, Outagamie County, Wis.

[73] Assignee: Kimberly-Clark Corporation, Neenah, Wis.

[21] Appl. No.: 32,833

[22] Filed: Mar. 30, 1987

[51] Int. Cl.$^4$ .............. A61F 13/20; B27N 5/02; B65D 3/04; F16L 11/00

[52] U.S. Cl. .......................... 604/11; 604/15; 138/144; 229/93; 428/34.2

[58] Field of Search .................. 604/1, 11, 13–18, 604/904, 367, 368, 370, 12; 138/144; 229/93; 428/35, 36; 128/157

[56] References Cited

U.S. PATENT DOCUMENTS

| | | | |
|---|---|---|---|
| 1,319,455 | 10/1919 | Bartlett | 229/93 |
| 3,170,489 | 2/1965 | Cunningham | 138/145 |
| 3,194,275 | 7/1965 | Biggs, Jr. et al. | 138/144 |
| 3,419,005 | 12/1968 | Lewing | 604/11 |
| 3,430,543 | 3/1969 | Cunningham | 138/144 |
| 3,468,733 | 9/1969 | Dunlap, Jr. et al. | 156/190 |
| 3,581,744 | 6/1971 | Voss et al. | 604/14 |
| 3,587,656 | 6/1971 | Cunningham | 138/144 |
| 3,670,731 | 6/1972 | Harmon | 604/368 |
| 3,813,026 | 4/1974 | Biancamaria | 229/93 |
| 3,844,315 | 10/1974 | Williams | 138/144 |
| 3,882,869 | 4/1975 | Hanke | 604/12 |
| 3,926,657 | 12/1975 | McConnell | 229/93 |
| 3,980,107 | 9/1976 | Barnes | 138/144 |
| 4,018,225 | 4/1977 | Elmi | 604/330 |
| 4,056,103 | 11/1977 | Kaczarzyk et al. | 604/904 |
| 4,077,408 | 3/1978 | Murray et al. | 604/15 |
| 4,102,340 | 7/1978 | Mesek et al. | 604/368 |
| 4,105,033 | 8/1978 | Chatterjee et al. | 604/368 |
| 4,117,184 | 9/1978 | Erickson et al. | 428/224 |
| 4,144,886 | 3/1979 | Holst et al. | 604/368 |
| 4,176,667 | 12/1979 | Herring | 604/368 |
| 4,186,238 | 1/1980 | Holst et al. | 428/326 |
| 4,192,827 | 3/1980 | Mueller et al. | 525/123 |
| 4,412,036 | 10/1983 | Pedersen et al. | 525/54.26 |
| 4,522,967 | 6/1985 | Sheldon | 524/377 |
| 4,540,454 | 9/1985 | Pieniak et al. | 156/62.2 |
| 4,592,751 | 6/1986 | Gegelys | 604/368 |
| 4,610,678 | 9/1986 | Weisman et al. | 604/368 |
| 4,650,459 | 3/1987 | Sheldon | 604/15 |

FOREIGN PATENT DOCUMENTS 0156649 10/1985 European Pat. Off. .
0533932 2/1947 United Kingdom .................. 229/93
1049894 11/1966 United Kingdom .

Primary Examiner—John D. Yasko
Assistant Examiner—Sharon Rose
Attorney, Agent, or Firm—Paul A. Leipold; Thomas J. Connelly

[57] ABSTRACT

The invention provides a tampon tube that is formed of a series of layers of paper, adhesive sealing means and superabsorbent material. The method of formation generally is to provide each of these materials in a sheet form and wind the tube convolutely with heat sealing during winding.

27 Claims, 2 Drawing Sheets

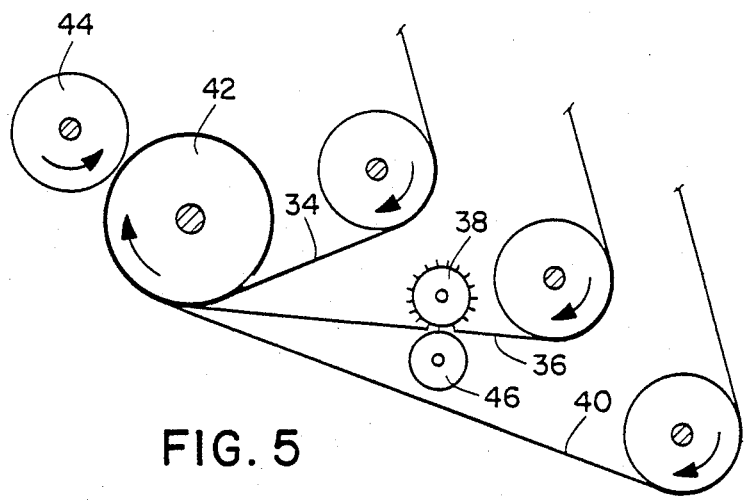
FIG. 5
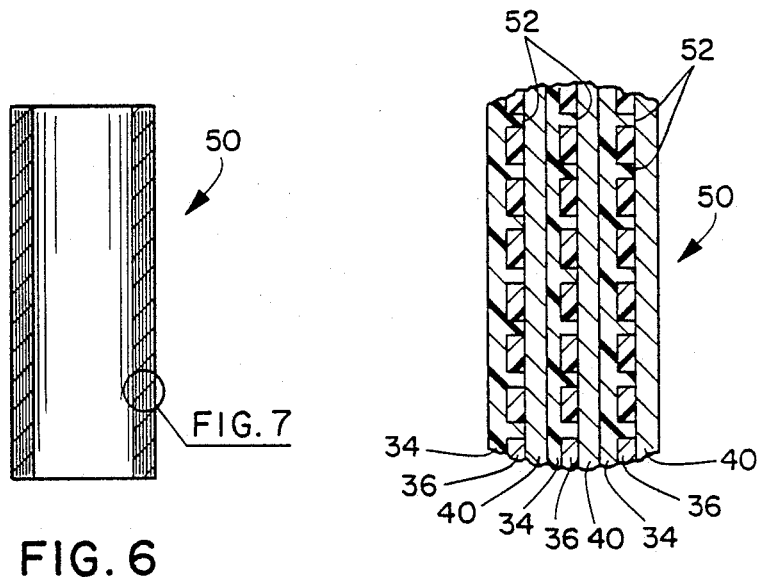
FIG. 6
FIG. 7

RAPIDLY DISINTEGRATING PAPER TUBES

TECHNICAL FIELD

This invention relates to paper tubes that disintegrate rapidly when placed in water. It particularly relates to applicators for catamenial tampons that will disintegrate when disposed of in a toilet and not obstruct plumbing when the toilet is flushed.

BACKGROUND ART

The catamenial tampon is a compressed cotton or other fibrous material that may be contained in a paper tube, plastic tube or mounted on a stick prior to use. With a paper tube or plastic tube tampon, the applicator normally has an inner and outer tube, with the inner tube being utilized to eject the tampon into the vagina from the outer tube. It is necessary that the paper tubes be formed stiff and strong enough for insertion and injection of the tampons into the vagina. However, when stiff, strong tubes of adhesively wrapped paper are disposed of in a toilet, the tubes will not rapidly disintegrate and are difficult to flush. As they are difficult to flush, it may lead to jamming of the pipes of the plumbing system.

It has been proposed in U.S. Pat. No. 3,419,005—Lewing that a wetting agent be added to the tube to aid in the disintegration of the tube. The addition of wetting agent is also proposed in United Kingdom Pat. No. 1,049,894—Robinson and Sons Limited, where the combination of a nonionic wetting agent and cetyl trimethyl ammonium bromide is proposed. It is also known to load the paper tubes with a mineral filler, such as calcium carbonate, to aid in the sinking of the tube into the toilet for better wetting. The formation of paper tubes may be carried out either with the formation of spiral-wound tubes, such as generally shown in U.S. Pat. No. 3,194,275—Biggs, Jr., et al. and U.S. Pat. No. 3,430,543—Cunningham. Also, it is known that tampon tubes may be formed by convolutely winding tubes such as disclosed in U.S. Pat. No. 4,650,459—Sheldon and U.S. Pat. No. 4,522,967—Sheldon.

However, there remains a need for a more rapidly disintegrating tube. There particularly remains a need for a tube that may be convolutely wound, is strong, low in cost and rapidly disintegrates.

DISCLOSURE OF THE INVENTION

An object of the invention is to overcome disadvantages of prior disintegratable tubes and methods of their formation.

A further object of the invention is to produce a rapidly disintegrating tampon tube that will be flushable.

Another additional object is to produce a low-cost method of forming water-disintegrating tampon tubes.

These and other objects of the invention are generally accomplished by providing a tampon tube that is formed of a series of layers of paper, adhesive sealing means and super-absorbent material. The method of formation generally is to provide each of these materials in a sheet form and wind the tube convolutely with heat sealing during winding.

BRIEF DESCRIPTION OF THE DRAWINGS

FIG. 5 is an alternate method and apparatus for forming an alternate embodiment of the tube of the invention.

FIG. 6 is a cross-section of a tube formed by the method of FIG. 5.

FIG. 7 is an enlarged view of the area designated FIG. 7 in FIG. 6.

MODES FOR CARRYING OUT THE INVENTION

The disposable tube of the invention has numerous advantages over prior tubes. The tube provides very rapid disintegration of the wrapped paper tube. Further, the tube has strength and stiffness as required for its use. The means used for disintegration of the tube does not interfere with the adhesive connection during forming. These and other advantages of the invention will be apparent from the detailed description below. The use of heat sealable webs in forming the tubes avoids handling of sticky liquid glue materials.

Figure 1:
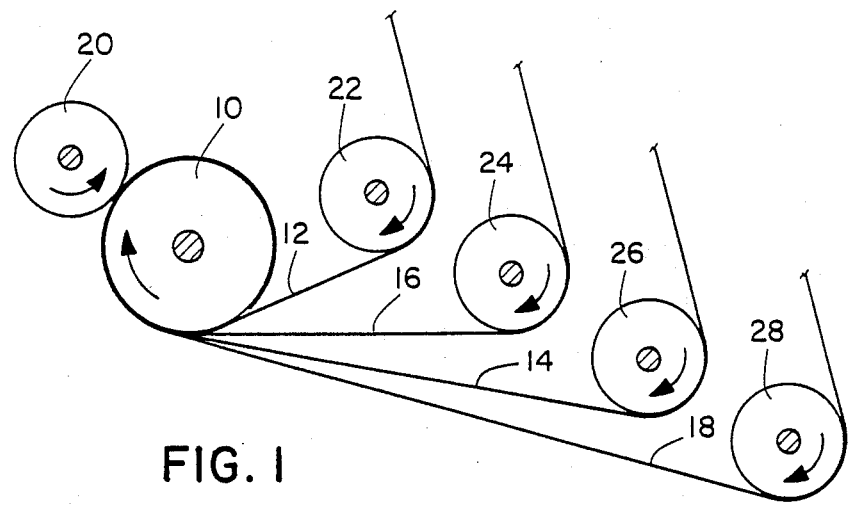
FIG. 1 is a schematic plan view of apparatus for forming the paper tube of the invention.
Figure 2:
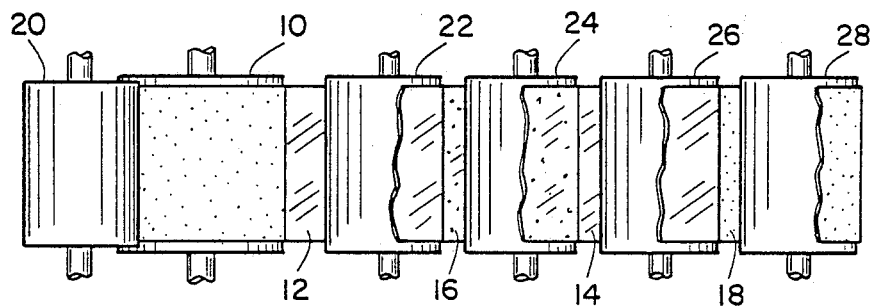
FIG. 2 is a top view of the apparatus and method of FIG. 1.

A method and apparatus for forming the tube of the invention is illustrated in FIGS. 1 and 2. The tube is wound on mandrel 10. The tube is wound from four webs. Webs 12 and 14 are heat-sealable films. Web 16 is a film of superabsorbent or superabsorbent impregnated carrier web. Web 18 is paper. These tubes are wrapped in layers onto mandrel 10 and sealed together by heated roll 20 bearing against mandrel 10. The webs are kept at constant tension during windings by the rolls 22, 24, 26 and 28.

Figure 3:
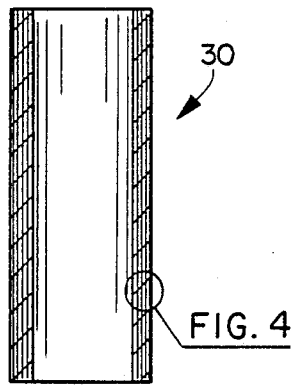
FIG. 3 is a cross-sectional view of a tube in accordance with the invention.
Figure 4:
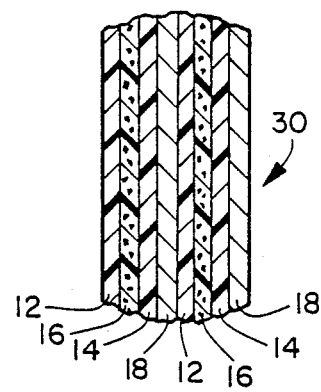
FIG. 4 is an enlarged view of the area designated FIG. 4 in FIG. 3.

The tube 30 illustrated in FIGS. 3 and 4 is composed of two complete windings of the webs of FIG. 1. The webs are held in place by the sealing of the heat-sealable webs 12 and 14. While illustrated with two layers, it is within the invention to wind more layers depending on the stiffness of the paper and the stiffness of the tube required to be formed.

In FIG. 5 there is illustrated an alternate embodiment of the invention. As illustrated in FIG. 5, the tube of the invention is composed of three layers of webs. Web 34 is a heat-sealable web. Web 36 is a superabsorbent web that is perforated by apparatus 38. Web 40 is paper. The webs are wound on mandrel 42 and fused by heating roll 44 bearing against the mandrel 42. Roll 46 is the backup roll for perforator 38.

FIGS. 6 and 7 illustrate a disposable tube made utilizing the alternate process of FIG. 5. As illustrated in FIGS. 6 and 7, the tube 50 has three thicknesses of webs 34, 36 and 40. The adhesive layer 34 has passed through the perforations 52 and joined the paper layers 40 directly together through the perforations of superabsorbent layer 36.

The paper utilized in forming the tubes of the invention may be any type that provides a tube of suitable properties of stiffness and cost. Generally, catamenial tubes are formed of a paper commonly referred to as groundwood base sheet. A preferred material is the 30 lb. free sheet of ground wood that has been provided with a slippery coating of high clay content. This material is preferred as the coating is slippery for ease of insertion and aids in disintegration and sinking of the tube as it is fast wetting. Further, the material is low in cost.

The adhesive web may be any of several known adhesive webs that will seal at temperatures that do not degrade the paper or the superabsorbent material. The adhesive may be any heat-sealable material that is capable of bonding at temperatures that do not degrade the paper or cardboard utilized. Typical of such materials are meltblown webs of polypropylene or polyethylene. One such material is a Sharnet ™ web of either polyester or polyamide resin composition. In one particularly preferred form of the invention, the adhesive may be a heat sealable and water soluble adhesive. The water soluble adhesive, combined with a superabsorbent, creates a particularly preferred material.

The superabsorbent sheet of the invention may be any suitable material that will quickly absorb water and swell, leading to disintegration of the tube. One advantage of the superabsorbent materials is that when they absorb water, they swell by a great amount, forcing the tube apart. As the tube is forced apart by swelling, more and more of the superabsorbent is exposed. Further, the swelling tends to break down the integrity of the tube, aiding in its being flushed. The webs of the superabsorbent of the invention may be other continuous webs of superabsorbent material or they may be material such as tissue carrier sheets that have been impregnated with a superabsorbent or laminated with powdered superabsorbent. Such materials are known in the art and generally are hydrogel materials that have the ability to absorb water but are crosslinked so as to not be water soluble. Such film materials are disclosed in U.S. Pat. No. 4,186,238—Holst et al., U.S. Pat. No. 4,117,184—Erickson et al., U.S. Pat. No. 2,192,827—Mueller, U.S. Pat. No. 4,212,036—Pedersen, U.S. Pat. No. 4,176,667—Herring, U.S. Pat. No. 4,592,751—Gegelys and U.S. Pat. No. 4,144,886—Holst et al.

The term superabsorbent as used herein is intended to mean the synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to render the materials substantially water insoluble. Cross-linking may, for example, be by irradiation or by covalent, ionic, Van der Waals, or hydrogen bonding. Suitable materials are available from various commercial vendors, such as Dow Chemical Company, Celanese Corporation, Allied-Colloid, and Stockhausen. The superabsorbent hydrogel material utilized in the invention is capable of absorbing at least about 15 times its weight in water, and preferably is capable of absorbing at least about 25-100 times its weight in water.

The following examples are intended to be illustrative and not exhaustive of the practice of the invention.

EXAMPLE I

A 3"×6" sheet of 30 lb. paper and a 3"×6" sheet of superabsorbent film interleaved with two 3"×6" sheets of Sharnet ™ polyester adhesive are convolutely wound into a tube. The paper is a relatively inexpensive grade from Midtec Paper, containing a high percentage of groundwood. The superabsorbent layer is commercially available film manufactured by Dow Chemical. The film is an acrylic absorbent film laminated between sheets of lightweight tissue with a dry weight of about 73 g/m$^2$. The adhesive is a commercially available heat sealable fibrous adhesive web from Sharnet Corp.

The sheets are convolutely wound on a Teflon-coated mandrel to form a tampon tube of 0.640" I.D. and 3" in length. The tube is sealed by rolling the mandrel on a hot plate at 400° F. for approximately 10 seconds as the tube is formed. The tube is then cooled to ambient temperature and dropped into a beaker of water. Initial delamination occurs in 5 minutes and total delamination time is 10 minutes.

EXAMPLE II

The procedure of Example I is repeated except a sheet of heat sealable, water soluble polyethyloxazoline adhesive of a composition as disclosed in U.S. Pat. No. 4,522,967—Sheldon et al. is substituted for the polyester adhesive. This use of a water soluble adhesive, in addition to the superabsorbent layer, results in an even faster delamination than the tube of Example I.

While the invention has been directed primarily to the formation of catamenial tampon tubes, it is also suitable for use in making other materials where rapid disintegration in water would be desirable. For instance, it could be utilized in the forming of toilet paper tubes or tubes that would be utilized on ships where waste is disposed of overboard. These and other products are intended to be included by the invention, the scope of which is to be limited only by the claims attached hereto.

We claim:

1. A wound tube, that has the strength and stiffness required for a tampon applicator tube and that will rapidly disintegrate in water comprising a plurality of layers of paper, binder and superabsorbent.

2. The tube of claim 1 wherein said paper, binder and superabsorbent comprise sheets that have been wound in layers.

3. The tube of claim 1 wherein said tube is convolutely wound.

4. The tube of claim 2 wherein the layer comprising superabsorbent also comprises a carrier material for said superabsorbent.

5. The tube of claim 1 wherein said tube is a tampon applicator tube.

6. The tube of claim 2 wherein said superabsorbent layer is perforated.

7. The tube of claim 2 wherein said binder comprises a sheet of thermoplastic meltblown material.

8. The tube of claim 2 wherein said paper comprises a ground wood sheet of about 30 pounds.

9. The tube of claim 2 wherein said paper is coated with a clay coating.

10. The tube of claim 7 wherein said meltblown is selected from the group comprising polypropylene and polyethylene.

11. The tube of claim 1 wherein said binder comprises polyethylene or polypropylene.

12. The tube of claim 1 wherein said binder comprises a water soluble adhesive sheet.

13. The tube of claim 2 wherein said superabsorbent sheet comprises a tissue sheet carrying particulate superabsorbent.

14. A tube that has the strength and stiffness required for a tampon applicator tube that will rapidly delaminate in water comprising wound sheets comprising at least one sheet of cellulose paper, at least one sheet comprising superabsorbent and at least one sheet of an adhesive that binds upon heating and cooling.

15. The tube of claim 14 wherein said tube is convolutely wound.

16. The tube of claim 14 wherein the sheet comprising superabsorbent also comprises a carrier material for said superabsorbent.

17. The tube of claim 14 wherein said tube is a tampon applicator tube.

18. The tube of claim 14 wherein said sheet comprising superabsorbent is perforated.

19. The tube of claim 14 wherein said adhesive comprises a sheet of thermoplastic meltblown material.

20. The tube of claim 14 wherein said paper comprises a ground wood sheet of about 30 pounds.

21. The tube of claim 14 wherein said sheet comprising superabsorbent comprises a tissue sheet carrying particulate superabsorbent.

22. A tampon tube that will rapidly delaminate in water comprising wound sheets comprising at least one sheet of cellulose paper, at least one sheet comprising superabsorbent and at least one sheet of a water soluble adhesive.

23. The tube of claim 22 wherein said tube is convolutely wound.

24. The tube of claim 22 wherein the sheet comprising superabsorbent also comprises a carrier material for said superabsorbent.

25. The tube of claim 22 wherein said tube is a tampon applicator tube.

26. The tube of claim 22 wherein the one sheet comprising superabsorbent is perforated.

27. The tube of claim 22 wherein said adhesive comprises a sheet of thermoplastic meltblown material.

* * * * *